(12) United States Patent
Jänsch et al.

(10) Patent No.: US 7,122,674 B2
(45) Date of Patent: Oct. 17, 2006

(54) PROCESS FOR PREPARING HIGH-PURITY HYDROXYINDOLYLGLYOXYLAMIDES

(75) Inventors: Hans-Joachim Jänsch, Radebeul (DE); Helge Hartenhauer, Dresden (DE); Hans Stange, Riesa (DE); Norbert Höfgen, Ottendorf-Okrilla (DE); Jürgen Schäfer, Radebeul (DE)

(73) Assignee: Elbion AG, Radebeul (DE)

( * ) Notice: Subject to any disclaimer, the term of this patent is extended or adjusted under 35 U.S.C. 154(b) by 364 days.

(21) Appl. No.: 10/631,475

(22) Filed: Jul. 31, 2003

(65) Prior Publication Data

US 2004/0063939 A1   Apr. 1, 2004

Related U.S. Application Data

(60) Provisional application No. 60/400,236, filed on Aug. 1, 2002.

(51) Int. Cl.
*C07D 401/04*  (2006.01)
*C07D 403/02*  (2006.01)
*C07D 209/04*  (2006.01)

(52) U.S. Cl. ............... 546/201; 548/181; 548/306.1; 548/454; 548/465

(58) Field of Classification Search ............ 548/181, 548/306.1, 465, 454; 546/201
See application file for complete search history.

(56) References Cited

U.S. PATENT DOCUMENTS

| 2,953,575 | A | * | 9/1960 | Erner et al. ............. 548/508 |
| 3,976,639 | A | | 8/1976 | Batcho et al. |
| 6,008,231 | A | | 12/1999 | Lebaut et al. |
| 6,251,923 | B1 | | 6/2001 | Hofgen et al. |

FOREIGN PATENT DOCUMENTS

| AU | 748403 B2 | 6/2002 |
| CH | 375 712 A | 3/1964 |
| DE | 198 18 964 A1 | 11/1999 |
| EP | 0 972 763 A1 | 1/2000 |
| GB | 1 276 966 | 6/1972 |

OTHER PUBLICATIONS

Abstract of "The Merck Index", Twelfth Edition (1996).*
1-Benzyl-gramin-derivate mit Serotonin-antagonistischer Wirkung, Ehrhart, et al. vol. 294, 1961, pp. 550-555.
Notiz Uber Einige Derivate dir '5-Benzyloxy-indolyl-(3)-glyoxysaure, Lipp, et al. vol. 91, 1958, pp. 242-243.

* cited by examiner

*Primary Examiner*—Golam M. M. Shameem
*Assistant Examiner*—Ebenezer Sackey
(74) *Attorney, Agent, or Firm*—Fulbright & Jaworski L.L.P.

(57) ABSTRACT

The invention relates to a process for preparing hydroxyindolylglyoxylamides in high yields and particularly pure form.

25 Claims, No Drawings

PROCESS FOR PREPARING HIGH-PURITY HYDROXYINDOLYLGLYOXYLAMIDES

This application claims priority of U.S. Provisional Application Ser. No. 60/400,236 filed Aug. 1, 2002.

TECHNICAL FIELD

The invention relates to a process for preparing substituted hydroxyindolylglyoxylamides of the general formula 1

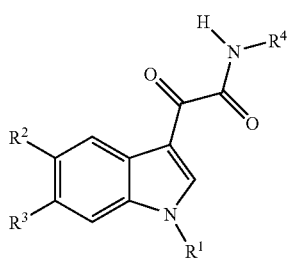

1 and of these in particular the compound AWD 12-281 (formula 2), which is a known inhibitor of phosphodiesterase 4 (PDE 4).

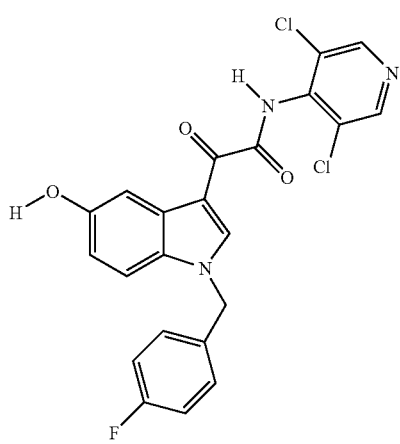

2

PRIOR ART

Processes for preparing various indol-3-ylglyoxylamides have already been described on several occasions. In all cases, indoles unsubstituted in position 3, which are synthesized by substitution in position 1 of a commercially available indole, were converted by reaction with oxalyl halides into indol-3-ylglyoxylyl halides which subsequently afford, by reaction with ammonia or with primary or secondary amines, the corresponding indol-3-ylglyoxylamides. (Scheme 1)

Scheme 1:

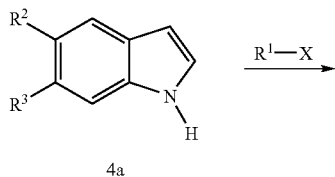

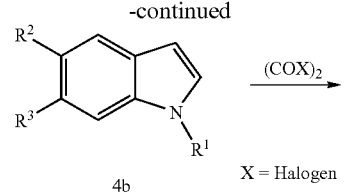

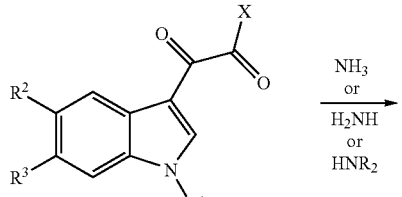

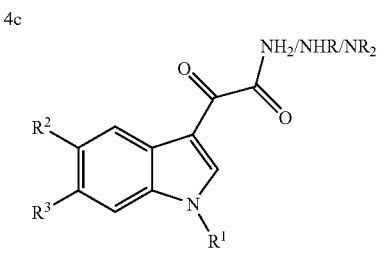

Thus, the patents U.S. Pat. No. 2,825,734 and U.S. Pat. No. 3,188,313 describe various indol-3-ylglyoxylamides which are prepared in the manner depicted in Scheme 1. These compounds are used as intermediates for preparing indole derivatives which are formed by reductions and which do not correspond to the general formula 1. This likewise applies to the indol-3-ylglyoxylamides described in U.S. Pat. No. 3,642,803.

The preparation of 5-methoxyindol-3-ylglyoxylamides is described in Farmaco 22 (1967), 229–244. The indole derivative used is again reacted with oxalyl chloride, and the resulting indol-3-ylglyoxylyl chloride is reacted with an amine.

In addition, U.S. Pat. No. 6,008,231 also describes indol-3-ylglyoxylamides and processes for preparing them. Once again, the reaction steps depicted in Scheme 1 are used. The described reaction conditions correspond to those utilized in the other sources.

A process for preparing substituted hydroxyindolylglyoxylamides was described for the first time in DE 198 18 964 A1. This entails use of indolylglyoxylamides of the formula 1 in which $R^2$ or $R^3$, or $R^2$ and $R^3$, are the —OR group, which were previously provided in the known manner shown in Scheme 1. The substituent —R is chosen so that the desired hydroxyindol-3-ylglyoxylamides are formed through elimination thereof. The substituent —R can in general be alkyl, cycloalkyl, arylalkyl, aryl, heteroaryl, acyl, alkoxycarbonyl, aryloxycarbonyl, aminocarbonyl, N-substituted aminocarbonyl, silyl, sulfonyl groups and complexing agents such as, for example, compounds of boric acid, of phosphoric acid, and metals bonded covalently or by coordination, such as zinc, aluminum or copper.

The substituent —R is eliminated by employing both acids and bases, such as, for example, hydrobromic acid, hydrochloric acid or hydroiodic acid, or sodium hydroxide solution, potassium hydroxide solution and sodium or potassium carbonate, but also activating Lewis acids such as, for example, AlCl$_3$, BF$_3$, BBr$_3$ or LiCl. The elimination reaction takes place in each case in the absence or in the presence of additional activators such as, for example, ethane-1,2-dithiol or benzyl mercaptan, and ether cleavages by means of hydrogen under elevated pressure or under atmospheric pressure in the presence of a suitable catalyst such as, for example, palladium or iridium catalysts.

The technical description of the use examples, in particular of the preparation of the compound 2, which is the substance AWD 12-281—a known PDE 4 inhibitor—has been concentrated on the elimination of a methyl or an acetyl group. In this connection, because of the superior yield, the elimination of the methyl group must be regarded as the preferred variant.

The previously known processes for preparing indol-3-ylglyoxylamides as shown in Scheme 1, and the subsequent elimination of suitable leaving groups as described in DE 198 18 964 A1 are suitable per se for preparing hydroxyindol-3-ylglyoxylamides of the formula 1 in the laboratory. However, the indole derivatives used as starting materials, such as, for example, methoxyindoles or acetoxyindoles, lead to considerable technical difficulties in applying the process for preparing these compounds in the quality necessary for a novel medicament. This applies especially to applications on a semi-industrial or industrial scale. Thus, the intermediates shown in Scheme 1, especially the 1-(4-fluorobenzyl) derivatives which are necessary for preparing AWD 12-281 (formula 2), are very difficult to isolate. For example, 1-(4-fluorobenzyl)-5-methoxyindole must be isolated by an extractive process in order to achieve a quality which can be used further industrially. Such elaborate processes inevitably also reduce the yield.

Irrespective of these technological disadvantages, it must be stated that the hydroxyindol-3-ylglyoxylamides of the formula 1 obtained after elimination of the leaving group —R as described in DE 198 18 964 A1 initially result as very impure products which can be brought into a pure form only by very elaborate isolation and working-up processes. This is mainly attributable to the unreacted precursor present in the product as main impurity, i.e. the portion in which —R has not been eliminated, and to the inorganic constituents present. In the case of R=methyl, the crude products are isolated by stirring the reaction solution with a sodium bicarbonate solution, during which the product separates out due to gradual neutralization. For R=acetyl, the basic reaction solution is neutralized with an acid, whereby the crude product separates out. To purify the crude products up to a quality necessary for active pharmaceutical ingredients, technically elaborate multiple recrystallizations from large volumes of solvent are necessary, together with a considerable requirement for reactor volume, which leads to considerable losses of yield and thus a low space-time yield.

It is thus an object of the invention to provide a simple process for preparing hydroxyindol-3-ylglyoxylamides of the formula 1, specifically AWD 12-281, in a particularly pure form necessary for pharmaceutical use.

DESCRIPTION OF THE INVENTION

The process of the invention relates to the preparation of hydroxyindol-3-ylglyoxylamides of the formula 1

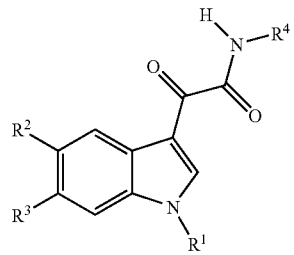

in which

R$^1$ is —C$_1$–C$_6$-alkyl, straight-chain or branched-chain, saturated or partially unsaturated, where appropriate substituted one or more times by mono-, bi- or tricyclic saturated or mono- or polyunsaturated carbocycles having 3–14 ring members or mono-, bi- or tricyclic saturated or mono- or polyunsaturated heterocycles having 5–15 ring members and 1–6 heteroatoms, which are preferably N, O and S, where the carbocyclic and heterocyclic substituents in turn may be substituted where appropriate one or more times by —OH, —SH, —NH$_2$, —NHC$_1$–C$_6$-alkyl, —N(C$_1$–C$_6$-alkyl)$_2$, —NHC$_6$–C$_{14}$-aryl, —N(C$_6$–C$_{14}$ aryl)$_2$, —N(C$_1$–C$_6$alkyl)(C$_6$–C$_{14}$aryl), —NO$_2$, —CN, —F, —Cl, —Br, —I, —O—C$_1$–C$_6$-alkyl, —O—C$_6$–C$_{14}$-aryl, —C$_1$–C$_6$-alkyl, —C$_6$–C$_{14}$-aryl or/and —COOH, where each C$_1$–C$_6$-alkyl residue on the carbocyclic and heterocyclic substituents may itself be substituted one or more times by —F, —Cl, —Br, —I, —OH or/and C$_6$–C$_{14}$-aryl, and where each C$_6$–C$_{14}$-aryl residue on the carbocyclic and heterocyclic substituents may itself be substituted one or more times by —F, —Cl, —Br, —I, —OH or/and C$_1$–C$_6$-alkyl, R$^2$, R$^3$ may be hydrogen or —OH, it being necessary for at least one of the two substituents to be —OH;

R$^4$ is a mono- or polycyclic aromatic carbocycle having 6–14 ring members or a mono- or polycyclic heterocycle having 5–15 ring members, where the heteroatoms are selected from N, O and S, where appropriate substituted one or more times by —F, —Cl, —Br, —I, —OH, —SH, —NH$_2$, —NH(C$_1$–C$_6$-alkyl), —N(C$_1$–C$_6$-alkyl)$_2$, —NH(C$_6$–C$_{14}$aryl), —N(C$_6$–C$_{14}$aryl)$_2$, —N(C$_1$–C$_6$-alkyl)(C$_6$–C$_{14}$-aryl), —NO$_2$, —CN, —O—C$_1$–C$_6$-alkyl, —O—C$_6$–C$_{14}$-aryl, —C$_1$–C$_6$alkyl, —C$_6$–C$_{14}$-aryl or/and —COOH, where each C$_1$–C$_6$-alkyl residue may itself be substituted one or more times by —F, —Cl, —Br, —I, —OH or/and —C$_6$–C$_{14}$-aryl and each C$_6$–C$_{14}$-aryl residue may itself be substituted one or more times by —F, —Cl, —Br, —I, —OH or/and C$_1$–C$_6$-alkyl.

The process comprises using 5-benzyloxyindole, 6-benzyloxyindole or 5,6-dibenzyloxyindole as starting materials.

R$^1$ is preferably a C$_1$–C$_3$-alkyl residue which is substituted where appropriate, such as, for example, n-propyl, isopropyl, cyclopentylmethyl or a benzyl residue which may itself be substituted one or more times by halogen, e.g. —F, —O—C$_1$–C$_6$-alkyl or —O—C$_1$–C$_6$-haloalkyl, e.g —OCH$_3$ or OCF$_3$, or/and —C$_1$–C$_6$-alkyl or C$_1$–C$_6$-haloalkzyl, e.g. —CH$_3$ or —CF$_3$.

R$^4$ is preferably a mono- or bicyclic aromatic carbocycles or heterocycles, especially N heterocycles.

R$^4$ is particularly prefered to be phenyl or pyridyl, in particular 4-pyridyl.

It is further preferred for $R^4$ to be substituted one or more times by —F, —Cl, —Br or/and I.

The most preferred compound is AWD 12-281 of formula 2.

The process of the invention preferably comprises the steps:
(a) reaction of the starting material 1a as shown in Scheme 1, in which $R^2$ and $R^3$ are hydrogen or a benzyl-protected OH, it being necessary for at least one of the two substituents to be a benzyl-protected —OH, with a compound $R^1$—X in which $R^1$ is as defined in claim 1, and X is halogen, to give a compound 1b as shown in Scheme 1;
(b) reaction of the compound 1b with a compound $(COX)_2$ in which X is halogen to give a compound 1c as shown in Scheme 1;
(c) reaction of the compound 1c with a compound selected from $NH_3$, $H_2NR$ and $HNR_2$ in which each R is independently any organic residue, e.g. as defined above for $R^1$, preferably with a compound $H_2NR$ in which R is as defined above for $R^4$, to give a compound 1d as shown in Scheme 1 and
(d) reaction of the compound 1d to give the target compound 1, comprising elimination of benzyl on $R^2$ and/or $R^3$ and, where appropriate (if not yet taken place in step (c)), introduction of the group $R^4$.

One advantage of the process of the invention is that the various intermediates as shown in Scheme 1 with R=benzyl can, in contrast to the previously preferred compounds with R=methyl or acetyl, be isolated in a technologically simple manner and, at the same time, result in a purity which makes purification steps for intermediates unnecessary.

In addition, the final products, mainly the hydroxyindol-3-ylglyoxylamides of the formula 1 can also be isolated in a very pure form from the reaction mixture in a novel manner, i.e. with distinctly less time exposure and expenditure on apparatus and materials, and thus very cost-effectively.

Thus, only small amounts of suitable solvents are necessary in order to prepare solutions from which the hydroxyindol-3-ylglyoxylamides of the formula 1 can be precipitated in a very pure form with acids. By contrast, in the prior art, very large volumes of solvent, e.g. 75 times the volume with heating for the product AWD 12-281, and addition of bases has been necessary.

However, isolation is also possible by adding small amounts of suitable solvents to a solution of hydroxyindol-3-ylglyoxylamides of the formula 1, heating and removing the products in very pure form while hot or after cooling.

Solvents suitable for the isolation of the invention are lower alcohols, e.g. $C_1$–$C_4$-alcohols, especially ethanol, alcohol mixtures or alcohol mixtures with water.

Small volumes of suitable solvents are preferably regarded as volumes up to 15 times the volume based on the isolated product. In use of pure alcohols, volumes up to 5 times the volume based on the isolated product are sufficient.

Bases suitable for dissolving the hydroxyindol-3-ylglyoxylamides of the formula 1 are bases suitable for the formation of solutions, such as sodium hydroxide solution or potassium hydroxide solution.

Acids suitable for the precipitation of the hydroxyindol-3-ylglyoxylamides of the formula 1 are mineral acids such as hydrochloric acid or low-cost organic acids such as acetic acid.

It is also possible to use both methods of isolation, i.e. dissolving the hydroxyindol-3-ylglyoxylamides of the formula 1 with addition of bases in small volumes of suitable solvents with subsequent precipitation and heating in small volumes of suitable solvents, removing while hot or cooling and removing, repeated or in combination, as described hereinafter by way of example.

Both variants for obtaining hydroxyindol-3-ylglyoxylamides in particularly pure form are suitable both for the laboratory, the semi-industrial and the industrial scale.

The processes of the invention are exceptionally well suited to the preparation of AWD 12-281 in particularly pure form.

The invention further relates to compounds of the general formulae 1b, 1c and 1d as depicted in the above scheme and to the use thereof as intermediates in the synthesis of compounds of the formula 1.

Exemplary Embodiments

The stages of the preparation and isolation process of the invention for preparing AWD 12-281 (2) in particularly pure form are described by way of example:

Stage 1: 5-benzyloxy-1-(4-fluorobenzyl)indole

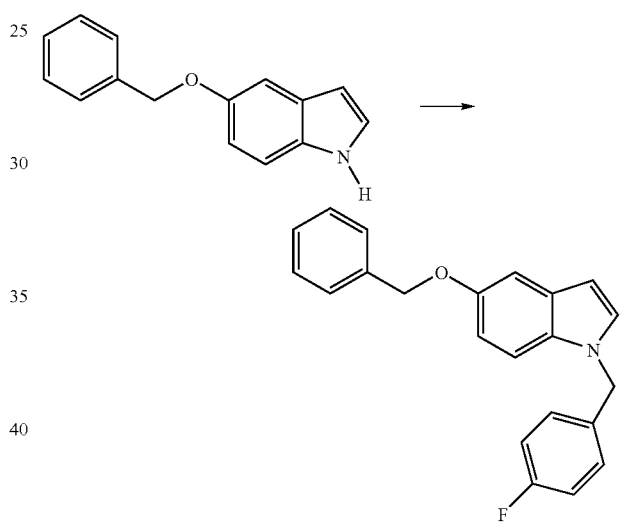

35.6 g of 5-benzyloxyindole, 94% pure (0.15 mol)
33.6 g of KOH pellets, ground in a mortar (0.6 mol)
26.0 g of 4-fluorobenzyl chloride (0.18 mol)
300 ml of DMF
1.5 ml of water The KOH pellets are added to the mixture of DMF and water, and the mixture is vigorously stirred for 5 minutes. After addition of the 5-benzyloxyindole, the mixture is stirred at room temperature for a further 45 minutes. Then, at an internal temperature of 10–20° C., 4-fluorobenzyl chloride is added dropwise while stirring. The mixture is then stirred at room temperature for a further 90 minutes. The mixture is cooled to 10° C., and 300 ml of water are added. It is cooled during this so that the internal temperature does not exceed 20° C. The mixture is stirred for 2 hours, and then the precipitate is filtered off with suction, washed with water and dried at 30° C. initially in circulating air and then in vacuo. The resulting product is very pure so that no additional purification operation is necessary.

Yield; 47.2 g (95% of theory) m.p.=77–78° C., colorless crystals

Stage 2: 5-benzyloxy-1-(4-fluorobenzyl)indol-3-ylglyoxylyl chloride

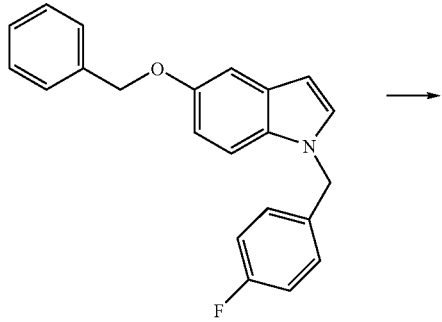

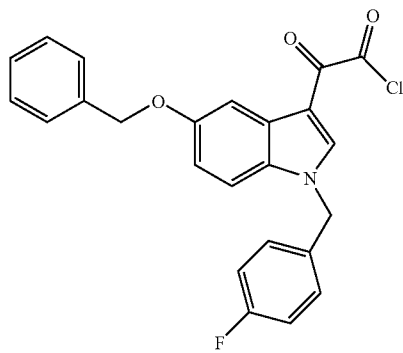

23.86 g of 5-benzyloxy-1-(4-fluorobenzyl)indole (0.072 mol)
9.90 g (7.2 ml) of oxalyl chloride (0.078 mol)
300 ml of tetrahydrofuran (dry)

A solution of 5-benzyloxy-1-(4-fluorobenzyl)indole in 200 ml of THF is cooled under a $N_2$ atmosphere to 0° C. While stirring and cooling further, a solution of oxalyl chloride in 100 ml of THF is added dropwise in such a way that the internal temperature does not exceed 10° C. The reaction mixture is then boiled under reflux for 2 hours. The solvent is distilled out as completely as possible in vacuo at a bath temperature of 50–60° C. The crude product remains as residue and crystallizes on cooling. It is employed without further working up in the next reaction stage.

Stage 3: N-(3,5-dichloropyrid-4-yl)-[5-benzyloxy-1-(4-fluorobenzyl)indol-3-yl]glyoxylamide

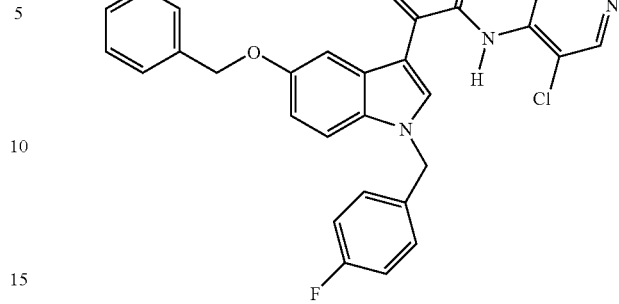

30.35 g of 5-benzyloxy-1-(4-fluorobenzyl)indol-3-ylglyoxylyl chloride (0.072 mol)
11.7 g of 4-amino-3,5-dichloropyridine (0.072 mol)
6.0 g of sodium hydride (60% in paraffin) (0.15 mol)
400 ml of tetrahydrofuran (dry)

The sodium hydride is introduced with stirring into 80 ml of THF. Then a solution of the 4-amino-3,5-dichloropyridine in 120 ml of THF is added dropwise. After the mixture has been stirred at room temperature for 1 hour it is cooled to an internal temperature of –5 to 0° C. While stirring, a solution of the 5-benzyloxy-1-(4-fluorobenzyl)indol-3-ylglyoxylyl chloride (crude product), obtained in the $2^{nd}$ stage, in 200 ml of THF is added dropwise. The reaction mixture is then boiled under reflux for 3 hours. The solvent is distilled out in vacuo. The residue is stirred with a mixture of 500 ml of water and 500 ml of ethyl acetate at 50° C. The phases are separated and the aqueous phase is washed with 100 ml of ethyl acetate. The combined organic phases are washed with 200 ml of water and then the solvent is distilled out in vacuo until a volume of about 200 ml remains. The product crystallizes out of the solution on cooling. It is filtered off with suction, washed with 15 ml of ethyl acetate and dried at 60° C. The filtrate is concentrated in vacuo until a volume of 50 ml remains. Further product crystallizes out on cooling and is washed and dried analogously.

Yield: 29.4 g (74% of theory, calculated for $2^{nd}$ and $3^{rd}$ stage) m.p.=155–158° C., yellow crystals Stage 4: N-(3,5-dichloropyrid-4-yl)-[1-(4-fluorobenzyl)-5-hydroxyindol-3-yl]glyoxylamide (AWD 12-281) (formula 2)

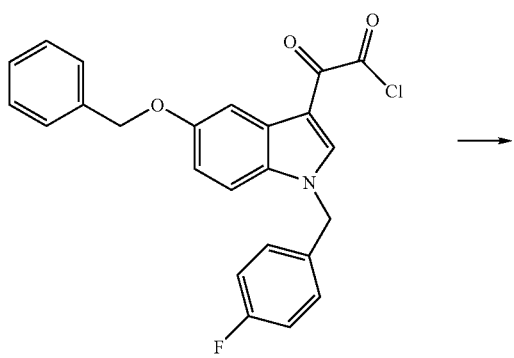

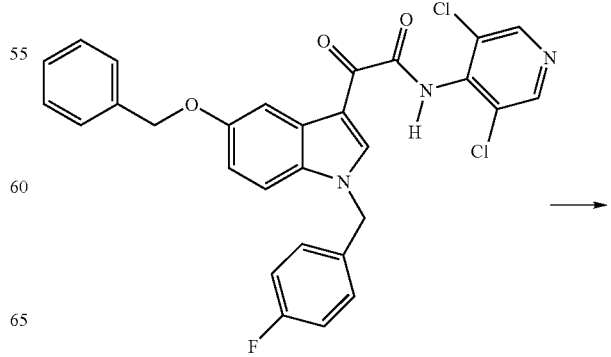

-continued

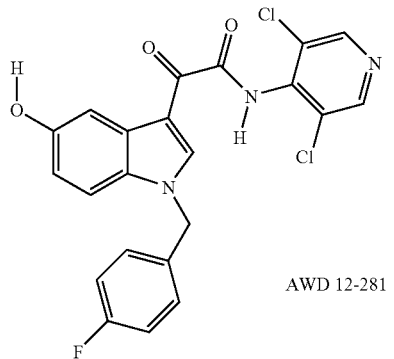

AWD 12-281

Variant a):
48 g of N-(3,5-dichloropyrid-4-yl)-[5-benzyloxy-1-(4-fluorobenzyl)indol-3-yl]glyoxylamide (0.0875 mol)
41.7 g of boron tribromide (0.166 mol)
530 ml of toluene
360 ml of water
50 ml of sodium hydroxide solution
720 ml of ethanol
57 ml of acetic acid 48 g of N-(3,5-dichloropyrid-4-yl)-[1-(4-fluorobenzyl)-5-benzyloxyindol-3-yl]glyoxylamide in 480 ml of toluene are heated to 60 to 70° C., 41.7 g of boron tribromide in 50 ml of toluene are added over the course of one hour, and the mixture is heated at 60 to 70° C. for 3 hours. It is cooled to about 20° C., 360 ml of water are added and, while cooling 50 ml of sodium hydroxide solution are added dropwise to dissolve the solid. The organic phase is separated off, the aqueous phase is extracted once more with 100 ml of toluene, and 720 ml of ethanol and 3.6 g of activated carbon are added to the aqueous phase. After filtration, the product is precipitated with 57 ml of acetic acid. It is filtered off with suction, washed with water and ethanol and dried. The yield is 34.1 g corresponding to 85% of theory.

Variant b);
40 g of N-(3,5-dichloropyrid-4-yl)-[5-benzyloxy-1-(4-fluorobenzyl)indol-3-yl]glyoxylamide (0.0873 mol)
36.3 g of boron tribromide (0.145 mol)
480 ml of toluene
330 ml of water
80 g of potassium carbonate 40 g of N-(3,5-dichloropyrid-4-yl)-[1-(4-fluorobenzyl)-5-benzyloxyindol-3-yl]glyoxylamide in 400 ml of toluene are heated to 70 to 80° C., 36.3 g of boron tribromide in 80 ml of toluene are added during the heating, and the mixture is heated at 75 to 80° C. for 3 hours. It is cooled to about 20° C. and a solution of 330 ml of water and 80 ml of potassium carbonate is added. The solid is filtered off with suction and washed with water and ethanol. The moist product is suspended in 400 ml of ethanol and dissolved by adding 20 ml of 5 N sodium hydroxide solution. The mixture is filtered, and the product is precipitated with 10 ml of hydrochloric acid. It is filtered off with suction, washed with water and then with ethanol and dried.

The yield is 30.0 g, corresponding to 90% of theory.

Variant c)
3.60 kg of N-(3,5-dichloropyrid-4-yl)-[5-benzyloxy-1-(4-fluorobenzyl)indol-3-yl]glyoxylamide (6.56 mol)
3.30 kg of boron tribromide (13.17 mol)
42 l of toluene
30 l of water
4.4 kg of potassium carbonate
24 l of ethanol 3.60 kg of N-(3,5-dichloropyrid-4-yl)-[1-(4-fluorobenzyl)-5-benzyloxyindol-3-yl]glyoxylamide in 36 l of toluene are heated to 75 to 80° C., 3.3 kg of boron tribromide in 6 l of toluene are added during the heating, and the mixture is heated at 75 to 80° C. for 3 hours. It is cooled to about 20° C. and a solution of 30 l of water and 4.4 kg of potassium carbonate is added. The solid is filtered off with suction and washed with 9 l of water and 3 l of ethanol. The moist product is boiled under reflux in 15 l of ethanol for 30 min. Cooling is followed by filtration with suction, washing with 6 l of ethanol and drying. The yield is 2.85 kg, corresponding to 95% of theory.

Use of each of these methods leads to AWD 12-281 in high purity. The particularly pure form of AWD 12-281 prepared by the process of the invention has a content above 98% and the total of all the impurities is never more than 0.5%. The content of the known main impurity N-(3,5-dichloropyrid-4-yl)-[5-benzyloxy-1-(4-fluorobenzyl)indol-3-yl]glyoxylamide is not more than 0.2% and inorganic constituents are removed to such an extent that their content, according to the determination of sulfated ash, is less than 0.1%.

Numerous other compounds of the formula 1 can be prepared in particularly pure form using the variants indicated by way of example, of which the following examples are mentioned;

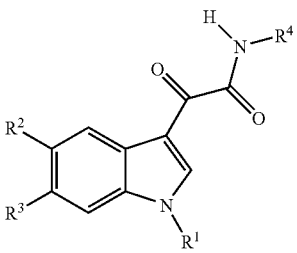

1

| Comp. | $R^1$ | $R^2$ | $R^3$ | $R^4$ | Melting point [° C.] |
|---|---|---|---|---|---|
| 3 | 2,6-difluorbenzyl | —OH | —H | 4-pyridyl | 327–329 |
| 4 | 2,6-difluoro-benzyl | —OH | —H | 3,5-dichloro-4-pyridyl | 266–268 |
| 5 | n-propyl | —OH | —H | 3,5-dichloro-4-pyridyl | 280–282 |
| 6 | isopropyl | —OH | —H | 3,5-dichloro-4-pyridlyl | 245–247 |
| 7 | cyclopentyl-methyl | —OH | —H | 3,5-dichloro-4-pyridyl | 246–248 |
| 8 | 4-fluorobenzyl | —OH | —H | 2,6-dichloro-phenyl | 216–218 |
| 9 | 4-fluorobenzyl | —OH | —H | 2,6-dichloro-4-trifluoro-methylphenyl | 199–201 |
| 10 | 4-fluorobenzyl | —OH | —H | 2,6-dichloro-4-trifluoro-methoxyphenyl | 176-178 |
| 11 | 4-fluorobenzyl | —H | —OH | 3,5-dichloro-4-pyridyl | 212–213 |
| 12 | 4-methoxy-benzyl | —OH | —H | 2,5-dichloro 4-pyridyl | 239–241 |

The invention claimed is:
1. A process for preparing a hydroxyindol-3-ylglyoxylamide of formula 1

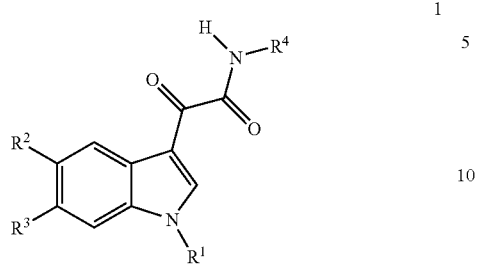

$R^1$ is —$C_1$–$C_6$-alkyl, straight-chain or branched-chain, saturated or partially unsaturated, where appropriate substituted one or more times by mono-, bi- or tricyclic saturated or mono- or polyunsaturated carbocycles having 3–14 ring members or mono-, bi- or tricyclic saturated or mono- or polyunsaturated heterocycles having 5–15 ring members and 1–6 heteroatoms, which are preferably N, O and S, wherein the carbocyclic and heterocyclic substituents are optionally substituted at least once with a substituent selected from the group consisting of —OH, —SH, —$NH_2$, —NH$C_1$–$C_6$-alkyl, —N($C_1$–$C_6$-alkyl)$_2$, —NH$C_6$–$C_{14}$-aryl, —N($C_6$–$C_{14}$aryl)$_2$, —N($C_1$–$C_6$alkyl)-($C_6$–$C_{14}$aryl), —$NO_2$, —CN, —F, —Cl, —Br, —I, —O—$C_1$–$C_6$-alkyl, —O—$C_6$–$C_{14}$-aryl, —$C_1$–$C_6$-alkyl, —$C_6$–$C_{14}$-aryl and —COOH, wherein each $C_1$–$C_6$-alkyl residue on the carbocyolic and heterocyclic substituents is optionally substituted at least once with a substituent selected from the group consisting of —F, —Cl, —Br, —I, —OH and $C_6$–$C_{14}$-aryl, and wherein each $C_6$–$C_{14}$-aryl residue on the carbocyclic and heterocyclic substituents is optionally substituted with —F, —Cl, —Br, —I, —OH and $C_1$–$C_6$-alkyl, wherein $R^2$ and $R^3$ are independently hydrogen, —OH or a benzyl -protected —OH, and wherein for formula 1 $R^2$ and $R^3$ are hydrogen or —OH and at least one of $R^2$ and $R^3$ are —OH, $R^4$ is a mono- or polycyclic aromatic carbocycle having 6–14 ring members or a mono- or polycyclic heterocycle having 5–15 ring members, where the heteroatoms are selected from N, O and S, wherein $R^4$ is optionally substituted at least once with —F, —Cl, —Br, —I, —OH, —SH, —$NH_2$, —NH($C_1$–$C_6$-alkyl), —N($C_1$–$C_6$-alkyl)$_2$, —NH($C_6$–$C_{14}$-aryl), —N($C_6$–$C_{14}$-aryl)$_2$, —N($C_1$–$C_6$-alkyl)($C_6$–$C_{14}$-aryl), —$NO_2$, —CN, —O—$C_1$–$C_6$-alkyl, —O—$C_6$–$C_{14}$-aryl, —$C_1$–$C_6$-alkyl, —$C_6$–$C_{14}$-aryl or —COOH, wherein each $C_1$–$C_6$-alkyl residue is optionally substituted at least once with —F, —Cl, —Br, —I, —OH or —$C_6$–$C_{14}$-aryl and each $C_6$–$C_{14}$-aryl residue is optionally substituted at least once with —F, —Cl, —Br, —I, —OH or $C_1$–$C_6$-alkyl, comprising:
(a) reacting a starting material of formula 1a

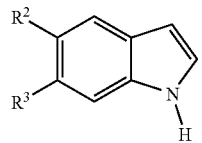

with a compound of formula $R^1$-X wherein X is halogen to form a compound of formula 1b

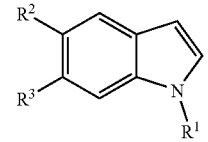

(b) reacting compound 1b with a compound of formula $(COX)_2$ wherein X is halogen to yield a compound of formula 1c

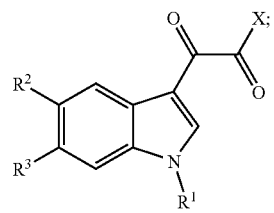

(c) reacting compound of formula 1c with a compound selected from $NH_3$, $H_2$NR and $HNR_2$; wherein R is —$C_1$–$C_6$-alkyl, straight-chain or branched-chain, saturated or partially unsaturated, where appropriate substituted one or more times by mono-, bi- or tricyclic saturated or mono- or polyunsaturated carbocycles having 3–14 ring members or mono-, bi- or tricyclic saturated or mono- or polyunsaturated heterocycles having 5–15 ring members and 1–6 heteroatoms, which are preferably N, O and S, wherein the carbocyclic and heterocyclic substituents are optionally substituted at least once with a substituent selected from the group consisting of —OH, —SH, —$NH_2$, —NH$C_1$–$C_6$-alkyl, —N($C_1$–$C_6$-alkyl)$_2$, —NH$C_6$–$C_{14}$-aryl, —N($C_6$–$C_{14}$aryl)$_2$, —N($C_1$–$C_6$alkyl)($C_6$–$C_{14}$aryl), —$NO_2$, —CN, —F, —Cl, —Br, —I, —O—$C_1$–$C_6$-alkyl, —O—$C_6$–$C_{14}$-aryl, —$C_1$–$C_6$-alkyl, —$C_6$–$C_{14}$-aryl and —COOH, where each $C_1$–$C_6$-alkyl residue on the carbocyclic and heterocyclic substituents is optionally substituted at least once with a substituent selected from the group consisting of —F, —Cl, —Br, —I, —OH and $C_6$–$C_{14}$-aryl, and wherein each $C_6$–$C_{14}$-aryl residue on the carbocyclic and heterocyclic substituents is optionally substituted with —F, —Cl, —Br, —I, —OH and $C_1$–$C_6$-alkyl, to yield a compound of formula 1d

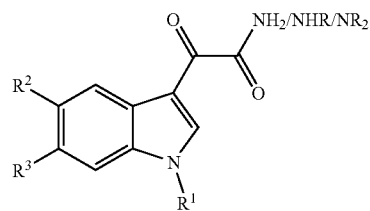

wherein for formulas 1a, 1b, 1c and 1d, $R^2$ and $R^3$ are hydrogen or a benzyl-protected —OH, and wherein at least one of $R^2$ and $R^3$ is a benzyl-protected —OH, (d) reacting the compound of formula 1d to yield a compound of formula 1 by removing a benzyl group on at least one of R² and R³ on formula 1d,
wherein said starting material is 5-benzyloxyindole, 6-benzyloxyindole or 5,6-dibenzyloxyindole.

2. The process as claimed in claim 1, wherein N-(3,5-dichloropyrid-4-yl)-[1-(4-fluorobenzyl)-5-hydroxyindol-3-yl]glyoxylamide (AWD 12-281) is prepared.

3. The process as claimed in claim 1, wherein 1-substituted 5-benzyloxy-, 6-benzyloxy- or 5,6-dibenzyloxyindoles of formula 1b as intermediates of stage (a) are employed without intermediate purification in the next stage (b) of the process.

4. The process as claimed in claim 3, wherein 5-benzyloxy-1-(4-fluorobenzyl)indole, the intermediate of stage (a) of the synthesis of AWD 12-281, is employed without any intermediate purification in the next stage (b) of the process.

5. The process as claimed in claim 1, wherein 1-substituted 5-benzyloxy-, 6-benzyloxy- or 5,6-dibenzyloxyindol-3-ylglyoxylyl chlorides of the formula 1c as intermediates of stage (b) are employed without intermediate purification in the next stage (c).

6. The process as claimed in claim 5, wherein 5-benzyloxy-1-(4-fluorobenzyl)indol-3-ylglyoxylyl chloride, the intermediate of stage (b) of the synthesis of AWD 12-281, is employed without intermediate purification in the next stage (c) of the process.

7. The process as claimed in claim 1, wherein 1-substituted 5-benzyloxy-, 6-benzyloxy- or 5,6-dibenzyloxyindol-3-ylglyoxylamides of the formula 1d of stage (c) are employed without intermediate purification in the next stage (d) of the process.

8. The process as claimed in claim 7, wherein N-(3,5-dichloropyrid-4-yl)-[5-benzyloxy-1-(4-fluorobenzyl)indol-3-yl]glyoxylamide, the intermediate of stage (c) of the synthesis of AWD 12-281, is employed without intermediate purification in the next stage (d) of the process.

9. The process as claimed in claim 1, wherein the reaction solution of the crude product stage (d) is purified by adjusting an alkaline pH at which the solution of the product is worked up by treatments which are customary per se, such as filtration or filtration in the presence of filtration aids.

10. The process as claimed in claim 9, wherein a pH of >9.5 is adjusted for purification of the reaction solution.

11. The process as claimed in claim 10, wherein a pH of >9.5 is adjusted for purification of the reaction solution of AWD 12-281.

12. The process as claimed in claim 9, wherein the purification of the reaction solution of stage (d) is followed by precipitation of the pure hydroxyindol-3-ylglyoxylamides of formula 1 by neutralization to a pH-value of 8 to 6 using organic or inorganic acids.

13. The process as claimed in claim 12, wherein hydrochloric acid is used for neutralization and precipitation of the pure hydroxyindol-3-ylglyoxylamides.

14. The process as claimed in claim 13, wherein the reaction solution of stage (d) of the synthesis of AWD 12-281 is, after the purification of this solution at alkaline pH, neutralized by adding hydrochloric acid to pH 8 to 6, whereupon the pure product precipitates.

15. The process as claimed in claim 1, wherein crude products of stage (d) of the process are dissolved in an alcohol with addition of a base, and this solution is worked up by treatments customary per se, such as filtration or filtration in the presence of filtration aids.

16. The process as claimed in claim 15, wherein ethanol and sodium hydroxide solution are used.

17. The process as claimed in claim 16, wherein ethanol and sodium hydroxide solution are used for working up the crude product of AWD 12-281.

18. The process as claimed in claim 15, wherein the pure hydroxyindol-3-ylglyoxylamides are, after working up the crude products, precipitated by adding an organic or inorganic acid up to a pH-value of 8 to 6.

19. The process as claimed in claim 18, wherein the pure hydroxyindol-3-ylglyoxylamides are, after working up the crude products, precipitated by adding hydrochloric acid up to a pH-value of 8 to 6.

20. The process as claimed in claim 19, wherein pure AWD 12-281 is, after working up the crude product, precipitated by adding hydrochloric acid up to a pH-value of 8 to 6.

21. The process as claimed in claim 1, wherein AWD 12-281 with a content of more than 98% is prepared.

22. The process as claimed in claim 1, wherein the total of all related impurities in AWD 12-281 is not more than 0.5%.

23. The process as claimed in claim 1, wherein the content of the main impurity N-(3,5-dichloropyrid-4-yl)-[5-benzyloxy-1-(4-fluorobenzyl)indol-3-yl]glyoxylamide in AWD 12-281 is not more than 0.2%.

24. A compound of formula

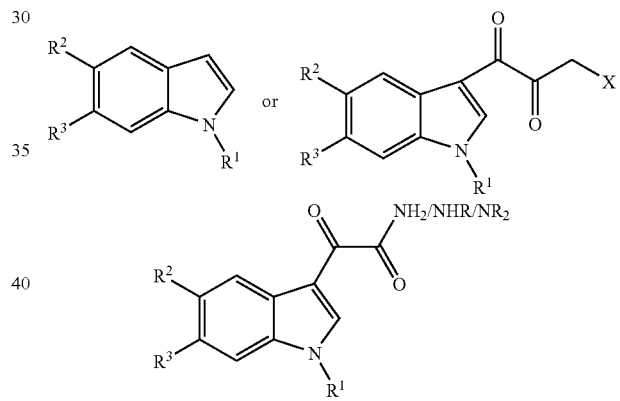

wherein R¹ is —$C_1$–$C_6$-alkyl, straight-chain or branched-chain, saturated or partially unsaturated, where appropriate substituted one or more times by mono-, bi- or tricyclic saturated or mono- or polyunsaturated carbocycles having 3–14 ring members or mono-, bi- or tricyclic saturated or mono- or polyunsaturated heterocycles having 5–15 ring members and 1–6 heteroatoms, which are preferably N, O and S, wherein the carbocyclic and heterocyclic substituents are optionally substituted at least once with a substituent selected from the group consisting of —OH, —SH, —$NH_2$, —$NHC_1$–$C_6$-alkyl, —$N(C_1$–$C_6$-alkyl$)_2$, —$NHC_6$–$C_{14}$-aryl, —$N(C_6$–$C_{14}$aryl$)_2$, —$N(C_1$–$C_6$alkyl)-($C_6$–$C_{14}$aryl), —$NO_2$, —CN, —F, —Cl, —Br, —I, —O—$C_1$–$C_6$-alkyl, —O—$C_6$–$C_{14}$-aryl, —$C_1$–$C_6$-alkyl, —$C_6$–$C_{14}$-aryl and —COOH, where each $C_1$–$C_6$-alkyl residue on the carbocyclic and heterocyclic substituents is optionally substituted at least once with a substituent selected from the group consisting of —F, —Cl, —Br, —I, —OH and $C_6$–$C_{14}$-aryl, and wherein each $C_6$–$C_{14}$-aryl residue on the carbocyclic and heterocyclic substituents is optionally substituted with —F, —Cl, —Br, —I, —OH and $C_1$–$C_6$-alkyl, wherein R is —$C_1$–$C_6$-alkyl, straight-chain or branched-chain, saturated or partially unsaturated, where appropriate substituted one or more times by mono-, bi- or tricyclic saturated or mono- or polyunsaturated carbocycles having 3–14 ring members or mono-, bi- or tricyclic saturated or mono- or polyunsaturated heterocycles having 5–15 ring members and 1–6 heteroatoms, which are preferably N, O and S, wherein the carbocyclic and heterocyclic substituents are optionally substituted at least once with a substituent selected from the group consisting of —OH, —SH, —$NH_2$, —$NHC_1$–$C_6$-alkyl, —$N(C_1$–$C_6$-alkyl$)_2$, —$NHC_6$–$C_{14}$-aryl, —$N(C_6$–$C_{14}$aryl$)_2$, —$N(C_1$–$C_6$alkyl)($C_6$–$C_{14}$aryl), —$NO_2$, —CN, —F, —Cl, —Br, —I, —O—$C_1$–$C_6$-alkyl, —O—$C_6$–$C_{14}$-aryl, —$C_1$–$C_6$-alkyl, —$C_6$–$C_{14}$aryl and —COOH, where each $C_1$–$C_6$-alky residue on the carbocyclic and heterocyclic substituents is optionally substituted at least once with a substituent selected from the group consisting of —F, —Cl, —Br, —I, —OH and $C_6$–$C_{14}$-aryl, and wherein each $C_6$–$C_{14}$-aryl residue on the carbocyclic and heterocyclic substituents is optionally substituted with —F, —Cl, —Br, —I, —OH and $C_1$–$C_6$-alkyl, wherein $R^2$ and $R^3$ are hydrogen or a benzyl-protected —OH and at least one of $R^2$ and $R^3$ is a benzyl-protected —OH; and wherein X is a halogen.

25. A method of preparing a hydroxyindol-3-ylglyoxylamide of formula 1

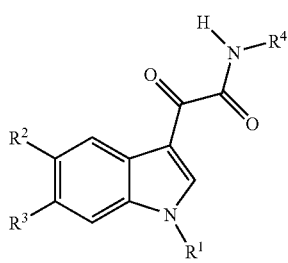

1

$R^1$ is —$C_1$–$C_6$-alkyl, straight-chain or branched-chain, saturated or partially unsaturated, where appropriate substituted one or more times by mono-, bi- or tricyclic saturated or mono- or polyunsaturated carbocycles having 3–14 ring members or mono-, bi- or tricyclic saturated or mono- or polyunsaturated heterocycles having 5–15 ring members and 1–6 heteroatoms, witch are preferably N, O and S, wherein the carbocyclic and heterocyclic substituents are optionally substituted at least once with a substituent selected from the group consisting of —OH, —SH, —$NH_2$, —$NHC_1$–$C_6$-alkyl, —$N(C_1$–$C_6$-alkyl$)_2$, —$NHC_6$–$C_{14}$-aryl, —$N(C_6$–$C_{14}$aryl$)_2$, —$N(C_1$–$C_6$alkyl)-($C_6$–$C_{14}$aryl), —$NO_2$, —CN, —F, —Cl, —Br, —I, —O—$C_1$–$C_6$-alkyl, —O—$C_6$–$C_{14}$aryl, —$C_1$–$C_6$-alkyl, —$C_6$–$C_{14}$-aryl and —COOH, wherein each $C_1$–$C_6$-alkyl residue on the carbocyclic and heterocyclic substituents is optionally substituted at least once with a substituent selected from the group consisting of —F, —Cl, —Br, —I, —OH and $C_6$–$C_{14}$-aryl, and wherein each $C_6$–$C_{14}$-aryl residue on the carbocyclic and heterocyclic substituents is optionally substituted with —F, —Cl, —Br, —I, —OH and $C_1$–$C_6$-alkyl, wherein $R^2$ and $R^3$ are independently hydrogen, —OH or a benzyl-protected —OH, and wherein for formula 1 $R^2$ and $R^3$ are hydrogen or —OH and at least one of $R^2$ and $R^3$ are —OH, $R^4$ is a mono- or polycyclic aromatic carbocycle having 6–14 ring members or a mono- or polycyclic heterocycle having 5–15 ring members, where the heteroatoms are selected from N, O and S, wherein $R^4$ is optionally substituted at least once with —F, —Cl, —Br, —I, —OH, —SH, —$NH_2$, —NH($C_1$–$C_6$-alkyl), —$N(C_1$–$C_6$-alkyl$)_2$, —NH($C_6$–$C_{14}$aryl), —$N(C_6$–$C_{14}$aryl$)_2$, —$N(C_1$–$C_6$-alkyl)($C_6$–$C_{14}$-aryl), —$NO_2$, —CN, —O—$C_1$–$C_6$-alkyl, —O—$C_6$–$C_{14}$-aryl, —$C_1$–$C_6$-alkyl, —$C_6$–$C_{14}$-aryl or —COOH, wherein each $C_1$–$C_6$-alkyl residue is optionally substituted at least once with —F, —Cl, —Br, —I, —OH or —$C_6$–$C_{14}$-aryl and each $C_6$–$C_{14}$-aryl residue is optionally substituted at least once with —F, —Cl, —Br, —I, —OH or $C_1$–$C_6$-alkyl, comprising (a) reacting a starting material of formula 1a

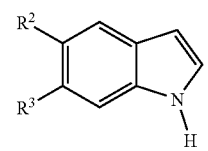

wherein $R^2$ and $R^3$ are hydrogen or a benzyl-protected OH, wherein at least one of $R^2$ and $R^3$ is a benzyl-protected —OH, with a compound of formula $R^1$-X wherein X is halogen to form a compound of formula 1b

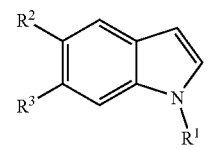

(b) reacting compound 1b with a compound of formula $(COX)_2$ wherein X is halogen to yield a compound of formula 1c

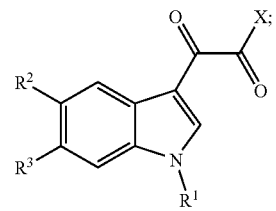

(c) reacting compound of formula 1c with a compound selected from $NH_3$, $H_2NR$ and $HNR_2$, wherein R is $—C_1–C_6$-alkyl, straight-chain or branched-chain, saturated or partially unsaturated, where appropriate substituted one or more times by mono-, bi- or tricyclic saturated or mono- or polyunsaturated carbocycles having 3–14 ring members or mono-, bi- or tricyclic saturated or mono- or polyunsaturated heterocycles having 5–15 ring members and 1–6 heteroatoms, which are preferably N, O and S.

wherein the carbocyclic and heterocyclic substituents are optionally substituted at least once with a substituent selected from the group consisting of —OH, —SH, $—NH_2$, $—NHC_1–C_6$-alkyl, $—N(C_1–C_6$-alkyl$)_2$, $—NHC_6–C_{14}$-aryl, $—N(C_6–C_{14}$ aryl$)_2$, $—N(C_1–C_6$alkyl$)$-$(C_6–C_{14}$aryl$)$, $—NO_2$, —CN, —F, —Cl, —Br, —I, $—O—C_1–C_6$-alkyl, $—O—C_6–C_{14}$-aryl, $—C_1–C_6$-alkyl, $—C_6–C_{14}$-aryl and —COOH, where each $C_1–C_6$-alkyl residue on the carbocyclic and heterocyclic substituents is optionally substituted at least once with a substituent selected from the group consisting of —F, —Cl, —Br, —I, —OH and $C_6–C_{14}$-aryl, and wherein each $C_6–C_{14}$-aryl residue on the cerbocyclic and heterocyclic substituents is optionally substituted with —F, —Cl, —Br, —I, —OH and $C_1–C_6$-alkyl, to yield a compound of formula 1d

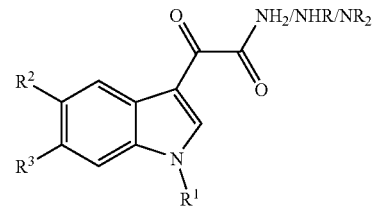

wherein for formulas 1a, 1b, 1c and 1d, $R^2$ and $R^3$ are hydrogen or a benzyl-protected —OH, wherein at least one of $R^2$ and $R^3$ is a benzyl-protected —OH, and (d) reacting the compound of formula 1d to yield a compound of formula 1 by removing a benzyl group on at least one of $R^2$ and $R^3$, wherein 5-benzyloxyindole, 6-benzyloxyindole or 5,6-dibenzyloxyindole is used as starting material and a compound of claim 24 is an intermediate in the process.

* * * * *